United States Patent [19]

Diamond et al.

[11] Patent Number: 4,689,341

[45] Date of Patent: Aug. 25, 1987

[54] ANTIARRHYTHMIC IMIDAZOLES

[75] Inventors: Julius Diamond, Mountain Lakes, N.J.; William C. Lumma, Jr., Pennsburg, Pa.; Thomas K. Morgan, Jr.; Ronald A. Wohl, both of Morris Plains, N.J.

[73] Assignee: Schering A.G., Berlin, Fed. Rep. of Germany

[21] Appl. No.: 881,760

[22] Filed: Jul. 3, 1986

Related U.S. Application Data

[60] Division of Ser. No. 675,172, Nov. 27, 1984, Pat. No. 4,613,609, which is a continuation-in-part of Ser. No. 513,143, Jul. 12, 1983, Pat. No. 4,581,370.

[30] Foreign Application Priority Data

Jul. 9, 1984 [EP] European Pat. Off. ........ 84108015.3

[51] Int. Cl.⁴ ............................................. A61K 31/415
[52] U.S. Cl. ..................................................... 514/399
[58] Field of Search ........................................ 514/399

[56] References Cited

FOREIGN PATENT DOCUMENTS 2030563 4/1980 United Kingdom ................ 514/399

Primary Examiner—Richard A. Schwartz
Attorney, Agent, or Firm—Elizabeth A. Bellamy; John L. White; I. William Millen

[57] ABSTRACT

The imidazolium salts described are useful as antiarrhythmic agents. A method of treating arrhythmia by increasing the refractoriness of cardiac tissue is provided as well as pharmaceutical formulations containing such imidazolium salts.

1 Claim, No Drawings

ANTIARRHYTHMIC IMIDAZOLES

CROSS REFERENCE TO RELATED APPLICATION

This application is a divisional of Ser. No. 675,172, filed Nov. 27, 1984, U.S. Pat. No. 4,613,609 which is a continuation-in-part of Ser. No. 513,143, filed July 12, 1983, U.S. Pat. No. 4,581,370.

FIELD OF THE INVENTION

This invention relates to novel quaternary salts and their use as antiarrhythmic agents. Specifically, this invention relates to imidazolium salts and their molecular compounds with aromatic dicarboxylic acids, pharmaceutical compositions containing them as active ingredients and to the method of using them for the treatment of arrhythmia. This invention also relates to certain intermediate substituted imidazoles useful as antiarrhythmic agents and pharmaceutical compositions containing them as active ingredients.

GENERAL DESCRIPTION OF THE INVENTION

Composition-of-Matter Aspect

In its composition-of-matter aspect, this invention relates to novel imidazolium salts. Particularly, this invention relates to the novel compounds defined by the following Formula I:

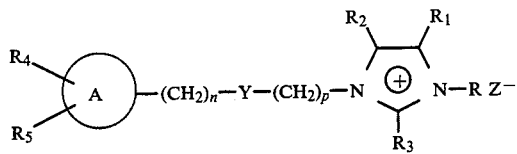

wherein
R is a straight or branched chain alkyl having 1-12 carbon atoms, cycloalkyl(lower)alkyl,

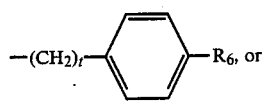

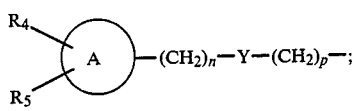

$R_1$, $R_2$, $R_3$ may be the same or independently, hydrogen, a straight chain alkyl group of 1-4 carbon atoms; $R_4$, $R_5$ may be the same or independently, hydrogen, halogen, hydroxy, lower alkyl, lower alkoxy, cyano, nitro, carbamoyl, lower alkylcarbamoyl, lower alkanoylamido, sulfamoyl, substituted sulfamoyl, sulfamoylamino, N-lower alkylsulfamoylamino, lower alkylsulfonamido, substituted lower alkylsulfonamido, trifluoromethanesulfonamido, ureido, N-lower alkylureido, or when taken together on adjacent carbon atoms of the ring to which they are attached may be joined to form the methylenedioxy moiety;
$R_6$ is hydrogen, halogen, hydroxy, cyano, carbamoyl, lower alkoxy, straight chain alkyl of 1-6 carbon atoms;
A is phenyl, furanyl, pyrrolyl, pyridinyl, thiazoyl, oxazolyl, the benzo derivatives of the foregoing and thiadiazolyl;
n is an integer of 0-2;
p is an integer of 0-5;
t is an integer of 1-5;
Y is methylene, hydroxymethylene, arylmethylene, substituted arylmethylene, phenylene, ethynylene,

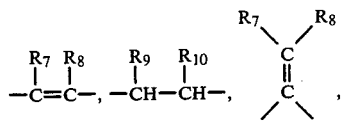

carbonyl, $>N-R_{11}$, $-NHSO_2-$, $-SO_2NH-$; wherein $R_7$, $R_8$ is hydrogen, $C_1-C_4$ lower alkyl or taken together form a 5 or 6 membered ring; $R_9$, $R_{10}$ is $C_1-C_4$ lower alkyl, or taken together may form a 5 or 6 membered ring or either may be hydrogen if the other is $C_1-C_4$ alkyl; $R_{11}$ is hydrogen, lower alkyl, cyano, carbamoyl; with the provisos that when:
(a) Y is $>N-R_{11}$, $-SO_2NH-$, $-NHSO_2-$, then p must be an integer of 2-5,
(b) Y is hydroxymethylene then R cannot be

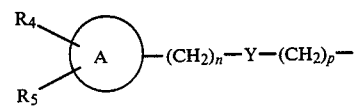

(c) Y is methylene, ethynylene,

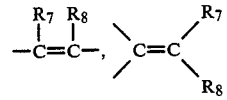

then p must be an integer of 1-5,
(d) the sum of the carbon atoms in the chain n, Y, p is 2 then both $R_4$ and $R_5$ cannot be hydrogen,
(e) Y is carbonyl then both $R_4$ and $R_5$ cannot be hydrogen;
$Z^-$ = halide, tosylate, sulfate, phosphate, methanesulfonate, and the molecular compounds of the foregoing quaternary salts with aromatic dicarboxylic acids.

In the above Formula I, halogen represents fluorine, chlorine bromine and iodine. The terms lower alkyl, lower alkoxy are taken to mean a straight or branched 1-4 carbon chain. Substituted sulfamoyl shall refer to lower alkyl substitution on the sulfamoyl nitrogen, which in turn may be substituted by a phenyl or lower alkoxy group and substituted lower alkylsulfonamido shall be taken to mean, phenyl or lower alkoxy substitution on the lower alkyl moiety. N-lower alkyluriedo shall be taken to mean lower

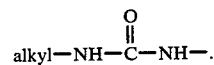

Preferred classes of compounds embodied by this invention are those of the above general formula having one or more of the following characteristics:
(1) A is phenyl and one of $R_4$ or $R_5$ is other than hydrogen (2) R is $C_7H_{15}$
(3) R is $CH_3$
(4) $R_3$ is $CH_3$ The following are some of the compounds which exemplify various aspects of the invention described herein.

(1) 1-[4-(4-Chlorophenyl)butyl]-3-heptylimidazolium chloride.
(2) 1-[4-(4-Chlorophenyl)butyl]-3-heptylimidazolium dihydrogenphosphate.
(3) 1-(4-Methoxyphenylpropyl)-3-methylimidazolium bromide.
(4) 1-Butyl-3-[3-(4-methoxyphenyl)propyl]imidazolium bromide.
(5) 1-[4-(4-Chlorophenyl)butyl]-3-heptylimidazolium chloride (1:1) compound with phthalic acid.
(6) 1-Heptyl-3-[3-(4-methoxyphenyl)propyl]imidazolium bromide.
(7) 1-Heptyl-3-[4-(methoxyphenyl)butyl]imidazolium bromide.
(8) 1-Heptyl-3-[4-(4-methoxyphenyl)butyl]-2-methylimidazolium bromide.
(9) 1-[3-((2,6-Dimethylphenyl)sulfamoyl)propyl]-3-heptylimidazolium chloride.
(10) (E)-1-[4-(4-Chlorophenyl)-2-butenyl]-3-heptylimidazolium chloride (1:1) compound with phthalic acid.
(11) 1-[4-(2,3-Dichlorophenyl)butyl]-3-heptylimidazolium chloride.
(12) 1-Heptyl-3-(4-phenylbutyl)imidazolium chloride 1:1 compound with phthalic acid.
(13) 1-[3-(4-Chlorophenyl)propyl]-3-heptylimidazolium chloride.
(14) 1-[4-(4-(Acetylamino)phenyl)butyl]-3-heptylimidazolium 4-methylbenzenesulfonate.
(15) 1-[4-(4-Chlorophenyl)butyl]-3-methylimidazolium chloride.
(16) 1-[4-(4-Chlorophenyl)butyl]-3-propylimidazolium dihydrogenphosphate.
(17) 1-[4,4-Diphenylbutyl]-3-heptylimidazolium dihydrogenphosphate.
(18) 1-[4-(4-Chlorophenyl)butyl]-3-(cyclohexylmethyl)imidazolium dihydrogenphosphate.
(19) 1-[4-(4-Fluorophenyl)butyl]-3-heptylimidazolium dihydrogenphosphate.
(20) 1-[4-(4-Chlorophenyl)butyl]-3-pentylimidazolium dihydrogenphosphate.
(21) 1-Butyl-3-[4-(4-chlorophenyl)butyl]imidazolium dihydrogenphosphate.
(22) 1-Heptyl-3-[4-[4-[[(methyl)sulfonyl]amino]phenyl]butyl]imidazolium dihydrogenphosphate.
(23) 1,3-bis [4-(4-Chlorophenyl)butyl]imidazolium dihydrogenphosphate.
(24) 1-[4-(4-Chlorophenyl)butyl]-3-(2-phenylethyl)imidazolium chloride.
(25) 1-[4-(4-Chlorophenyl)-1-methylbutyl]-3-heptylimidazolium 4-methylbenzenesulfonate.
(26) 1-[4-(4-Chlorophenyl)-(E)-3-butenyl]-3-heptylimidazolium chloride.
(27) 1-[4-(2,3-Dichlorophenyl)-2-butenyl]-3-heptylimidazolium 4-methylbenzenesulfonate.
(28) 1-[4-(2-Chlorophenyl)-2-butenyl]-3-heptylimidazolium dihydrogenphosphate.
(29) 1-[4-(4-Chlorophenyl)-3-butynyl]-3-heptylimidazolium 4-methylbenzenesulfonate.
(30) 1,2-Dimethyl-3-[4-[4-[[methanesulfonyl]amino]phenyl]butyl]-imidazolium methanesulfonate.
(31) 1-[4-(2-Chlorophenyl)butyl]-3-heptylimidazolium dihydrogenphosphate.
(32) 1-[4-(4-Chlorophenyl)butyl]-3-(2-methylpropyl)imidazolium chloride.
(33) 1-[4-(4-Chlorophenyl)butyl]-3-heptyl-2-methylimidazolium dihydrogenphosphate.
(34) 1-[4-(4-Chlorophenyl)butyl]-2,3-dimethylimidazolium chloride.
(35) 1-Heptyl-3-[4-(4-methoxyphenyl)butyl]-2,4,5-trimethylimidazolium bromide.
(36) 1-[4-(4-fluorophenyl)-2-oxobutyl]-3-heptylimidazolium chloride.
(37) 1-[5-(4-Chlorophenyl)pentyl]-3-heptylimidazolium dihydrogenphosphate.
(38) 1-[2-Hydroxy-2-[4-[(methanesulfonyl)amino]phenyl]ethyl]-3-methylimidazolium iodide.
(39) 1-Heptyl-3-[2-[4-[(methanesulfonyl)amino]phenyl]-2-oxoethyl]imidazolium bromide.
(40) 1-[2-((2,6-Dimethylphenyl)sulfamoyl)ethyl]-3-heptylimidazolium bromide.
(41) (E)-1-[4-(4-Fluorophenyl)-3-butenyl]-3-heptylimidazolium dihydrogenphosphate.
(42) (Z)-1-[4-(4-Chlorophenyl)-2-butenyl]-3-heptylimidazolium dihydrogenphosphate.
(43) 1-Methyl-3-[2-[4-((methylsulfonyl)amino)phenyl]ethyl]-1H-imidazolium iodide.
(44) 1-Methyl-3-[2-[4-((methylsulfonyl)amino)phenyl]-2-oxoethyl]-1H-imidazolium bromide.
(45) 1-Methyl-3-[3-[4-((methylsulfonyl)amino)phenyl]-3-oxopropyl]-1H-imidazolium chloride.
(46) 1,2-Dimethyl-3-[2-[4-((methylsulfonyl)amino)phenyl]-2oxoethyl]-1H-imidazolium chloride.
(47) 1,2-Dimethyl-3-[2-hydroxy-2-[4-((methylsulfonyl)amino)phenyl]ethyl]-1H-imidazolium chloride.
(48) 1-[2-[4-((Ethylsulfonyl)amino)phenyl]-2-oxoethyl]-3-methyl-1H-imidazolium chloride.
(49) 1-(1-Methylethyl)-3-[2-[4-((methylsulfonyl)amino)phenyl]-2-oxoethyl]imidazolium chloride.
(50) 1-[2-Hydroxy-2-[4-((methylsulfonyl)amino)phenyl]ethyl]-3-(1-methylethyl)-1H-imidazolium chloride.
(51) 1-[3-Hydroxy-3-[4-((methylsulfonyl)amino)phenyl]propyl]-3-methyl-1H-imidazolium chloride.
(52) 1-Ethyl-3-[2-hydroxy-2-[4-((methylsulfonyl)amino)phenyl]-1H-imidazolium chloride.
(53) 1-[2-[4-((Ethylsulfonyl)amino)phenyl]-2-hydroxyethyl]-3-methyl-1H-imidazolium chloride.
(54) 1-Ethyl-3-[2-[4-((methylsulfonyl)amino)phenyl]-2-oxoethyl]-1H-imidazolium chloride.
(55) 1-Methyl-3-[3-[4-((methylsulfonyl)amino)phenyl]propyl]-1H-imidazolium chloride.
(56) (−)-1-[2-Hydroxy-2-[4-((methylsulfonyl)amino)phenyl]-ethyl]-3-methyl-1H-imidazolium chloride.
(57) (+)-1-[2-Hydroxy-2-[4-((methylsulfonyl)amino)phenyl]-ethyl]-3-methyl-1H-imidazolium chloride.

Among the compounds as defined by Formula I, a site for stereo or geometric isomerism may exist, e.g. asymmetric carbon atoms or olefinic linkages. Any of the optical and cis/trans isomers so possible are considered to be part of this invention.

Another aspect of this invention are the molecular compounds of the quaternary salts of Formula I with aromatic dicarboxylic acids. Representative of such acids are phthalic acid, 1,8-naphthalenedicarboxylic acid, 1,2-naphthalenedicarboxylic acid and 2,3-naphthalenedicarboxylic acid.

A further aspect of this invention are certain intermediate substituted imidazoles which have been found to have antiarrhythmic activity. Such compounds are defined by the following Formula II:

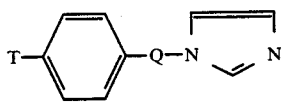

wherein T is selected from the group consisting of nitro, amino, lower alkanesulfonamido, and Q is selected from the group consisting of a straight chain alkyl of 1–4 carbon atoms,

—CHOHCH$_2$—, and the pharmaceutically acceptable acid addition salts thereof. Representative of the compounds of Formula II are the following:
(1) 1-[4-(4-Nitrophenyl)butyl]imidazole hydrochloride
(2) N-[4-(1H-Imidaz-1-ylacetyl)phenyl]methanesulfonamide
(3) 2-(1H-Imidaz-1-yl)-1-(4-nitrophenyl)ethanone hydrochloride
(4) N-[4-(1-Hydroxy-2-(1H-imidazol-1-yl)ethyl]-phenyl]methanesulfonamide
(5) 1-(4-Aminophenyl)-2-(1H-imidazol-1-yl)ethanone
(6) α-(4-Nitrophenyl)-1H-imidazole-1-ethanol
(7) N-[4-[2-(1H-Imidazol-1-yl)ethyl]phenyl]methanesulfonamide
(8) 1-[2-(4-Nitrophenyl)ethyl]-1H-imidazole hydrochloride
(9) (+)-1-[2-Hydroxy-2-[4-((methylsulfonyl)amino)-phenyl]-ethyl]-1H-imidazole d-7,7-dimethyl-2-oxobicyclo[2.2.1]-heptane-1-methanesulfonic acid salt
(10) (1)-1-[2-Hydoxy-2-[4-((methylsulfonyl)amino)-phenyl]-ethyl]-1H-imidazole 1-7,7-dimethyl-2-oxobicyclo[2.2.1]-heptane-1-methanesulfonic acid salt
(11) (−)-1-[2-Hydroxy-2-[4-((methylsulfonyl)amino)-phenyl]-ethyl-1H-imidazole In the foregoing Formula II lower alkyl defines a straight or branched chain of 1–4 carbon atoms. The pharmaceutically acceptable acid addition salts contemplated are prepared according to known procedures and are those derived from, for example, the following acids; hydrochloric, hydrobromic, sulfuric, phosphoric, acetic, propionic, benzoic, naphthoic, oxalic, succinic, maleic, malic, adipic, lactic, tartaric, citric, salicyclic, methanesulfonic and p-toluenesulfonic.

PROCESS ASPECT

The compounds of this invention may be prepared in general, by various processes and reactants known in the art. In order to produce the compounds according to Formula I and those intermediates of Formula II the following schemes were most usually employed.

In one schematic route, in order to produce a 1-substituted imidazole, combine one equivalent of an alkyl halide (or tosylate) or alternatively a substituted aralkyl halide (or tosylate) with 2–5 equivalents of imidazole. Heat the mixture neat or in a suitable solvent (e.g. acetonitrile, nitromethane, dimethylformamide) at from about 80° to about 150° C. Follow the progress of the reaction by thin-layer chromatography. When the reaction is completed, remove the solvent (if one used) in vacuo and dissolve the resultant reaction mixture in 5 to 10 volumes of water. If necessary, adjust the pH of the solution to pH 9 with aqueous base. Extract the aqueous mixture with methylene chloride, which is washed with water, dried over sodium sulfate and evaporated. In such a manner the 1-alkylimidazole or alternatively the 1-(substituted aralkyl)-imidazole may be prepared.

Still another method for preparing the foregoing compounds is as follows. To 1.1 equivalents of sodium hydride in anhydrous 1,2-dimethoxyethane with about 1.1 equivalents of dimethylformamide in an atmosphere of nitrogen add about one equivalent of imidazole. Heat the reaction mixture to reflux. When the evolution of hydrogen has ceased, add the appropriate halide (or tosylate) slowly to the reaction mixture and when the addition is completed, continue heating and follow the progress of the reaction by thin-layer chromatography. When complete, quench the reaction mixture in ice water. Extract the aqueous mixture with methylene chloride, and as above, the appropriate 1-substituted imidazole is produced.

Generally, the 1,3-disubstituted imidazolium salts may be prepared as follows. Combine one equivalent of the 1-substituted imidazole with at least one or more equivalents of the alkyl halide (or tosylate) or substituted aralkyl halide (or tosylate). Heat the mixture neat or in a suitable solvent (e.g. acetonitrile, dimethylformamide or nitromethane) at about 80° to about 150° C. Follow the reaction by thin-layer chromatography and when complete, dissolve the reaction mixture (after removal of the solvent, if used, in vacuo) in water and adjust the pH of the solution with saturated sodium bicarbonate to about pH 8. Extract the aqueous solution several times with ether, then adjust the pH of the aqueous component with a suitable acid (same anion as that of the imidazolium salt) to about pH 3. Extract the aqueous layer with methylene chloride, after drying and evaporation of the solvent the appropriate imidazolium salt is produced.

It will be apparent to those skilled in the art that certain of the substituted aralkyl halides etc. are available commercially and still others may be prepared by variants on known processes.

One expeditious route to the substituted aralkyl halides especially in the case where the alkyl is an alkenyl moiety would be the diazotization of a suitably substituted aniline, and reacting it to a Meerwein arylation with copper chloride, copper bromide or copper sulfate and a butadiene to produce the substituted arylbutenyl chloride, bromide or alcohol which latter compound can be converted to the tosylate ester.

The following schematics are illustrative of ways to produce the compounds of the invention:

A.
B.
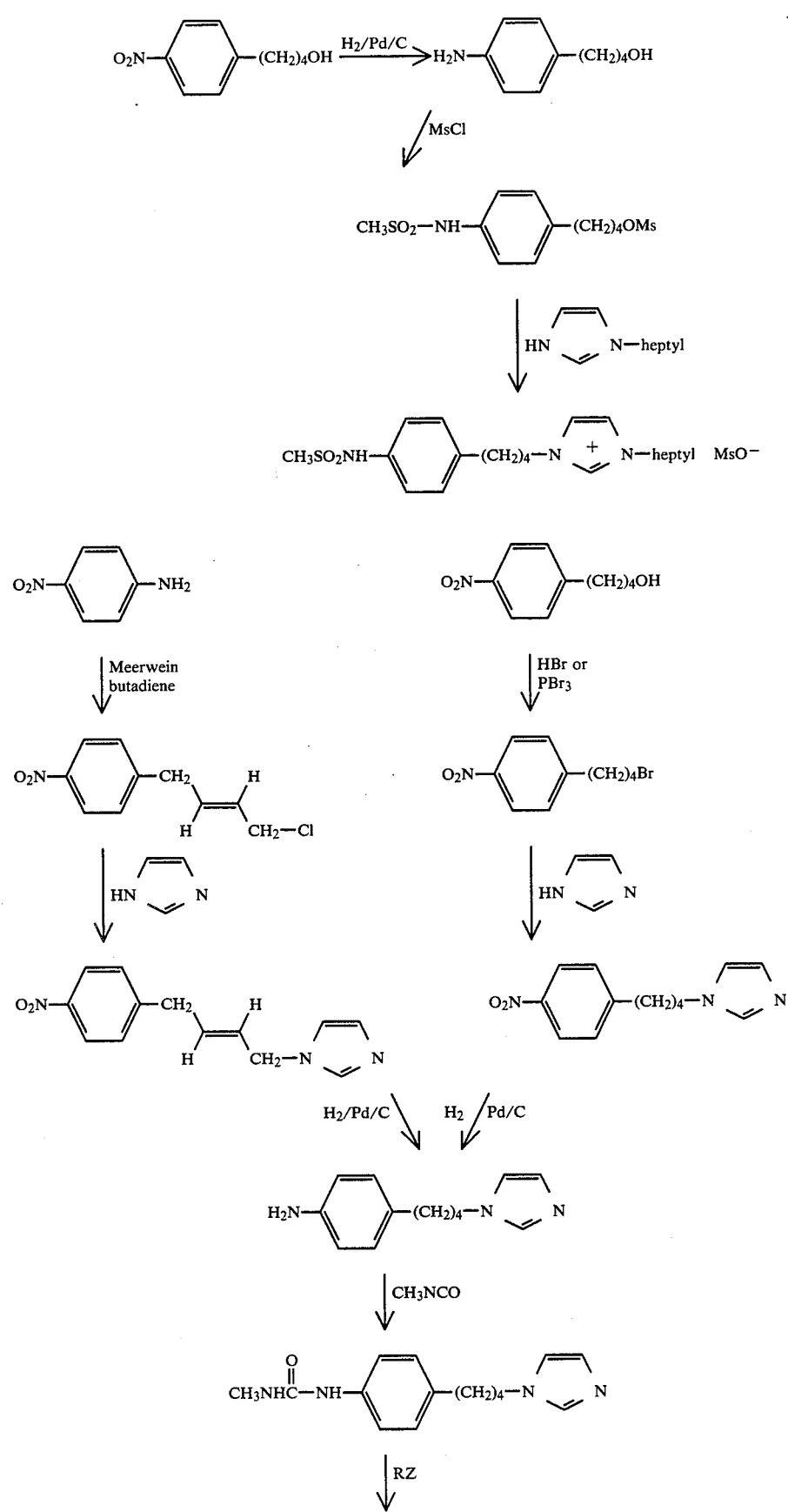

-continued

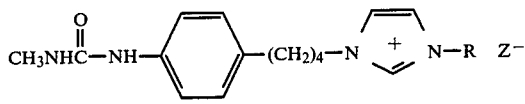

If it is necessary or desirable to change the anion, this may be accomplished by commercially available ion exchange resins. As for instance, the chloride anion may be exchanged in an anion exchange resin (e.g. Biorad AG-1-X8, 20-50 mesh hydroxide form) and the resulting eluates titrated with 10% phosphoric acid to produce the $H_2PO_4^-$ anion.

METHOD-OF-USE AND PHARMACEUTICAL COMPOSITION ASPECT

The quaternized imidazoles of this invention, their molecular compounds with aromatic dicarboxylic acids and certain of the unquaternized imidazoles and their pharmaceutically acceptable acid addition salts have been found to increase refractoriness of cardiac tissue thereby providing their usefulness as antiarrhythmic agents. Their activity has been analyzed in several procedures such as, utilizing standard electro-physiological techniques to measure resting potential, action potential amplitude, duration, rate of rise and refractory periods of normal canine Purkinje fibres; and also utilizing the programmed electrical stimulation conscious dog model.

The primary method for evaluating these compounds as antiarrhythmic agents was an in vitro electro-physiological screen using canine Purkinje fibers. Using conventional microelectrode techniques the effects of the drugs on the action potential characteristics of the Purkinje fiber were measured. Both Class I and Class III antiarrhythmic agents can be disinguished using this method. For a compound to be considered active as a Class III agent it must have prolonged the action potential duration at 95% repolarization ($APD_{95}$) by 20% without affecting conduction properties. A decrease in the rate of rise of phase 0 (Vmax) by 20% was considered a toxic effect on conduction for a Class III agent as well as being the criterion for activity for a Class I antiarrhythmic agent.

$C_{10}APD_{95}$—the concentration of drug (in micromolar units) which causes a 10% increase or decrease (−) in $APD_{95}$ from control value $C_{20}APD_{95}$—the concentration of drug (in micromolar units) which causes a 20% increase or decrease (−) in $APD_{95}$ from control value MaxAPD$_{95}$ (conc.)—the maximum observed effect on $APD_{95}$ from control value and the concentration (in micromolar units) where this occurred Vmax (conc.)—the change (+,−) in the rate of rise of phase 0 of the action potential from control value and the concentration of drug which caused the observed change NR—not reached
NE—no effect The above data were recorded for a normal stimulated beat at a basic cycle length of 1000 milliseconds.

The $C_{10}APD_{95}$ information is included here because some compounds which caused a 10% prolongation of $APD_{95}$ but which did not cause a 20% prolongation in $APD_{95}$ were shown to be effective in an in vivo dog model.

The following Table I illustrates the activity of some of the compounds.

TABLE I

| | In Vitro (Canine Purkinje Fiber Studies) | | | |
|---|---|---|---|---|
| Compound No. | $C_{10}APD_{95}$ ($\mu M$) | $C_{20}APD_{95}$ ($\mu M$) | MaxAPD$_{95}$ (conc) | Vmax (conc) |
| I-1 | (+) 12 | | 27% (30) | −20% (15) |
| I-7 | 0.5 | 8 | 26% (10) | −12% (10) |
| I-12 | 20 | NR | | −20% (10-30) |
| I-14 | 13 | 30 | 21% (30) | increased |
| I-16 | 6.0 | NR | 11% (10) | −20% (>10) |
| I-19 | 1.0 | 10 | 20% (10) | −6% (10) |
| I-20 | 0.8 | 6.0 | 23% (10) | NE |
| I-21 | 2.0 | 6 | 25% (10) | NE |
| I-22 | 1.3 | 3.0 | 39% (10) | Minimal |
| I-25 | 10 | NR | 10% (10) | NE |
| I-29 | 20 | NR | 15% (30) | −20% (20) |
| I-30 | 1.0 | 7.0 | 23% (10) | NE |
| I-34 | 1.4 | 6.0 | 25% (10) | NE |
| I-38 | 0.3 | 0.8 | 63% (10) | −5% (10) |
| I-39 | 1.7 | 9.0 | 21% (10) | NE |
| I-42 | 38 | | 12% (100) | −26% (100) |
| I-43 | 2.0 | 8.0 | 21% (10) | NE |
| I-44 | 1.0 | 2.3 | 38% (10) | NE |
| II-1 | 1.2 | 4.0 | 27% (10) | NE |
| II-2 | 3.0 | 14.0 | 67% (100) | −15% (100) |
| II-3 | 20.0 | 50.0 | 29% (100) | NE |
| II-4 | 2.0 | 7.0 | 23% (10) | −15% (10) |
| II-5 | 4.0 | NR | 13% (10) | Minimal |
| II-6 | 15.0 | 43.0 | 28% (100) | NE |
| II-7 | 2.0 | 10.0 | 47% (100) | NE |
| II-8 | 7.0 | 30.0 | 29% (100) | −15% (0.1) |

Thus there is provided by this invention a method for treating arrhythmia which comprises administering to a subject suffering from an arrhythmia and in need of treatment or to a subject suspected of developing an arrhythmia an effective amount for treating such arrhythmia of a compound of this invention. The compounds are preferably utilized for the control of reentrant arrhythmias in humans and for the prevention of sudden death resulting from ventricular fibrillation. Accordingly, it is contemplated that the compounds are best utilized in prophylactic treatment. Moreover, since the compounds enhance the electrical stability of the heart, they can be used in conjunction with electrical devices designed to terminate cardiac arrhythmias such as ventricular tachycardia and ventricular fibrillation.

In general, the compounds of this invention may be administered orally or parenterally. The dosage administered will be dependent on the subject being treated, the route of administration and the type and severity of the arrhythmia being prevented or reduced.

A typical dose for prophylactic treatment, however, will contain from about 0.5 mg/kg to about 5 mg/kg of the active compounds of this invention when administered orally. For I.V. administration, the dose will be from about 0.2 mg/kg to about 4 mg/kg, preferably about 0.2 to about 2 mg/kg.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention for example, 1-[4-(4-chlorophenyl)butyl]-3-heptylimidazolium dihydrogenphosphate or 2-(1H-imidaz-1-yl)-1-(4-nitrophenyl)-ethanone hydrochloride in the amount of about 10 to about 50 mg. Such formulation can be administered orally at the rate of about 1 or 2 capsules per day or more often as needed depending upon the particular condition and subject being treated.

For parenteral administration a compound of this invention can be formulated for intramuscular or intravenous administration. In the case of treatment of a patient suffering from a severe cardiac arrhythmia, it may be desirable to administer a compound of the invention by intravenous infusion in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or saline solution, buffered aqueous solutions as well as dispersing and surface active agents if necessary. A typical formulation suited to intramuscular administration may contain one of the compounds of this invention such as 1-[4-(4-chlorophenyl)-2-butenyl]-3-heptylimidazolium chloride (1:1) phthalic acid or 2-(1H-imidaz-1-yl)-1-(4-nitrophenyl)ethanone hydrochloride in the amount of about 10 to 250 mg and a solubilizing agent and sufficient sterile water to bring the volume to about 2 ml. Such formulation can be injected at a rate of 1 to 4 times per day or more often depending upon the particular condition of the subject being treated.

The pharmaceutical preparations of the compounds of this invention may optionally, additionally contain one or more other pharmaceutically active substances. Some of the substances envisioned are vasodilators such as glycerol trinitrate, pentaerythritol tetranitrate and carbochromene; diuretic agents, such as chlorothiazide; heart tonics, such as digitalis preoarations; hypotensive agents, such as Rauwolfia alkaloids and guanethidine; bronchodilators and sympathomimetic agents, such as isoprenaline, orciprenaline, adrenalin and ephedrine; α-adrenergic blocking agents, such as phentolamine; β-adrenergic blocking agents, such as propranolol and other antiarrhythmic agents such as quinidine.

Other utilities may be ascribed to certain of the quaternized imidazoles of this invention, e.g. cardiotonic agents, bradycardic agents, antifungal agents and stabilizers for physiological formulations such as ophthalmic drops.

This invention described hereinabove is illustrated below in the Examples, which, however, are not to be construed as limiting the scope of this invention.

PREPARATION 1

Acetic Acid, 4-[4-(Acetylamino)phenyl]butyl ester

To a solution of 30.0 g (0.15 mole) of 4-(p-nitrophenyl)-butanol in 375 ml glacial acetic acid add 30.9 g (0.55 mole) of iron filings. Stir the suspension at reflux for 5½ hrs, following the progress of the reaction by thin-layer chromatography on silica gel (acetonitrile: ammonium hydroxide, 90:10). At the completion of the reaction, pour the reaction mixture onto 3 liters of ice water and extract with 3×300 ml of chloroform. Combine the organic layers and wash with 100 ml water. Dry the chloroform extracts over potassium carbonate, filter and concentrate in vacuo to give an oily solid. Recrystallize from 400 ml ether to obtain the title compound.

NMR (CDCl$_3$): δ=1.50-1.85 (m, 4), 2.04 (s, 3), 2.14 (s, 3), 2.60 (t, 2), 4.06 (t, 2), 6.92-7.55 (m, 4) and 7.90(br s, 1)ppm.

PREPARATION 2

4-(Acetylamino)benzenebutanol

To a solution of 19.3 g (0.077 mole) of acetic acid, 4-[4-(acetylamino)phenyl]butyl ester in 300 ml of ethanol, add a solution of 21 g potassium carbonate in 300 ml of water. Heat the resulting solution at 55° C. for 4 hrs. following the progress of the reaction by thin-layer chromatography on silica gel (acetonitrile: ammonium hydroxide, 90:10). At the completion of the reaction, filter off any insolubles and remove the ethanol in vacuo. Extract the aqueous residue with 3×300 ml methylene chloride Wash the combined organic layers with 100 ml water, dry over potassium carbonate, filter and remove the solvent in vacuo. Recrystallize the resulting solid from 140 ml acetonitrile to obtain the title compound.

NMR (CDCl$_3$): δ=1.50-1.90 (m, 4), 1.75 (s, 2, exchange), 2.15 (s, 3), 2.45-2.80 (m, 2), 3.65 (t, 2) and 7.00-7.60 (m, 4)ppm.

PREPARATION 3

4-Methylbenzenesulfonic acid, 4-4-(acetylamino)ohenyl]butyl ester

To a 0° C. solution of 4.5 g (0.022 mole) 4-(acetylamino)-benzenebutanol in 25 ml pyridine, add 8.3 g (0.044 mole) tosyl chloride and chill in the refrigerator overnight. Follow the progress of the reaction by thin-layer chromatography on silica gel (acetonitrile: ammonium hydroxide, 90:10). At the completion of the reaction, pour the reaction mixture onto 500 ml ice water and stir for 15 minutes. Extract the aqueous mixture with 3×300 ml ether. Wash the combined organic layers with 1N hydrochloric acid, then with water, dry over potassium carbonate, filter and remove the solvent in vacuo to obtain the title compound.

NMR (CDCl$_3$) δ=1.40-2.00 (m, 4), 2.10 (s, 3), 2.40 (s, 3), 2.30-2.80 (m, 2), 4.00 (t, 2) and 6.90-7.90 (m, 8)ppm.

PREPARATION 4

1-Heptyl-2,4,5-trimethyl-1H-imidazole

Dissolve 16.0 g (0.019 mole) of 2,4,5-trimethyl-1H-imidazole hydrochloride in 125 ml dry N,N-dimethylformamide and cool to 0° C. Add 8.75 g (0.218 mole) of sodium hydride (60%), stir at 0° C. for 30 minutes and then heat reaction mixture to 100° C. for one hour. Cool to 0° C. and then add 18.0 ml (0.114 mole) of n-heptyl bromide to reaction mixture. Upon completion of addition, heat to 100° C. for four hours, following the progress of the reaction by thin-layer chromatography on silica gel (methanol: 1M sodium chloride, 95:5). At the completion of the reaction, cool to room temperature and add 2 ml water. Filter precipitated salts and evaporate solvent.

Dissolve this residue in 200 ml 10% NaOH and then extract into methylene chloride (200 ml). Evaporate solvent and then distill in vacuo to obtain the title compound.

NMR (CDCl$_3$): δ=0.90 (t, 3), 1.1–1.7 (m, 10), 2.1 (s, 6), 2.4 (s,3) and 3.76 (t, 2)ppm.

PREPARATION 5

1-Chloro-4-ethynylbenzene

Dissolve 276.5 g (0.634 mole) of bromomethyltriphenyl phosphonium bromide in 1800 ml THF and cool to −78° C. Add 67.6 g (0.062 mole) potassium tert.-butoxide and stir at −78° C. for 2 hours. Add 89.12 g p-chlorobenzaldehyde in 200 ml THF to cold reaction mixture and stir for 30 minutes. Add 142.3 g potassium tert.-butoxide and then allow to warm to room temperature. After 18 hours, add 500 ml saturated aqueous ammonium chloride solution and 500 ml H$_2$O and extract with 500 ml diethyl ether. Wash organic layer with 2×400 ml saturated aqueous sodium chloride solution, dry over magnesium sulfate, filter and evaporate solvent. Wash residue with 200 ml hexane and filter off precipitate. Evaporate hexane and dissolve material in 150 ml hexane:methylene chloride (66:33) solution and elute through column containing 300 g silica gel (Merck 60-230 mesh) with hexane:methylene chloride (66:33) solution. Monitor column chromatography using thin-layer chromatography on silica gel (hexane:methylene chloride, 66:33). Collect desired fraction and evaporate solvent. Distill residue in vacuo and collect fraction boiling at 65° C. (8.5mmHg) to obtain the title compound.

PREPARATION 6

4-(4-Chlorophenyl)-3-butyn-1-ol

Dissolve 14.2 g (0.104 mole) of 1-chloro-4-ethynylbenzene in 35 ml dry THF and cool to −78° C. Add 49 ml butyl lithium to cold reaction mixture and allow to warm to room temperature for 2 hours. After 2 hours, cool to −78° C. and the add 5.8 ml (0.114 mole) ethylene oxide in 20 ml THF. Allow to warm to room temperature. Monitor progress of reaction with thin-layer chromatography on silica gel (methylene chloride). After 18 hours, add 150 ml saturated aqueous ammonium chloride solution and extract with 150 ml diethyl ether. Wash organic layer with 2×100 ml saturated aqueous sodium chloride solution. Dry organic layer with magnesium sulfate and then filter, and evaporate solvent to obtain the title compound.

PREPARATION 7

4-(4-Chlorophenyl)-3-butyn-1-ol 4-methylbenzenesulfonate (Ester)

Dissolve 13.3 g (0.0736 mole) of 4-(4-chlorophenyl)-3-butyn-1-ol in 70 ml pyridine and cool to 0° C. Add 16 g (0.0837 mole) of p-toluenesulfonyl chloride and stir in ice bath for one hour. Store in freezer over night. Add 200 ml diethyl ether and then wash with 3×150 ml 1N hydrochloric acid. The organic layer is then washed with 50 ml saturated aqueous sodium bicarbonate solution and then dried over magnesium sulfate. Evaporate solvent to obtain the title compound.

NMR (CDCl$_3$): δ=2.42 (s, 3), 2.77 (t, 2), 4.17 (t, 2), 7.21 (s, 4), 7.31(d, 2) and 7.82(d,2)ppm.

PREPARATION 8

4-(Methanesulfonylamino)benzenebutanol methanesulfonate (Ester)

9.25 g (0.056 mole) 4-aminobenzenebutanol is dissolved in 100 ml pyridine and the solution is cooled to ca. −10° C. 17.33 ml (25.65 g) (0.244 mole) methanesulfonyl chloride is added dropwise with vigorous stirring at a rate such that the methanesulfonyl chloride is added, the reaction mixture is left in the freezer for two days. The reaction mixture is poured onto 300 ml ice water and extracted with 3×200 ml methylene chloride. The combined organic layers are washed with 1 liter cold 5% HCl in 3 portions. The organic layer is dried over sodium sulfate, filtered, and stripped. The residue is crystallized from ethyl acetate/ether to obtain the title compound.

NMR (CDCl$_3$) δ=1.56–1.93 (m, 4), 2.47–2.82 (m, 2), 2.98 (s,3), 3.02 (s, 3), 4.07–4.42 (m, 2), 7.20 (s, 4) and 7.25 (br s, 1)ppm.

PREPARATION 9

2,3-Dichlorophenyldiazonium chloride

To a suspension of 25 g (0.15 mole) 2,3-dichloroaniline in 16 ml H$_2$O, add 39 ml (0.46 mole) concentrated HCl. Stir the mixture at room temperature for about five minutes. Cool the mixture to −5° to 0° C. and add dropwise a solution of 11 g (0.16 mole) NaNO$_2$ in 30 ml H$_2$O. Stir the resulting solution at −5° to 0° C. for about 30 minutes, then filter the solution into an ice-cooled filter flask. Keep the filtrate containing the diazonium salt at about 0° C.

PREPARATION 10

1-Chloro-4-(2,3-dichlorophenyl)-2-butene

Suspend 12.3 g (0.09 mole) NaOAc·3H$_2$O and 4.6 g (0.03 mole) CuCl$_2$ in 160 ml acetone and 25 ml H$_2$O. Cool the mixture to −5° to 0° C. Add 12.4 g (20 ml, 0.23 mole) of condensed butadiene. Add the solution of 2,3-dichlorophenyldiazonium chloride dropwise, keeping the diazonium salt solution and the reaction mixture between −5° and 5° C. at all times. When the addition is complete, discontinue cooling, and stir the reaction mixture at room temperature for about 16 hours.

Add 160 ml diethyl ether to the reaction mixture and stir at room temperature for about five minutes. Separate the layers, and wash the organic layer with 2×150 ml H$_2$O and 150 ml saturated NaCl solution. Dry the organic layer over MgSO$_4$. Evaporate the solvent, and distill the resulting oil to obtain the title compound.

NMR(CDCl$_3$) δ=3.52(d, 2), 4.05(d, 2), 5.01–6.27 (m, 2) and 7.04–7.52 (m, 3)ppm.

PREPARATION 11

Cyclopropyl-4-fluorophenylmethanone

Add 20.0 g (0.10 mole) γ-chloro-p-fluorobutyrophenone dropwise to a methanolic KOH solution (prepared from 9.8 g of 86% KOH pellets and 60 ml of methanol). Stir the mixture at room temperature for 40 minutes and pour into 100 ml of water and then extract with 3×30 ml of methylene chloride. Wash the methylene chloride extracts with 3×40 ml of water, dry over magnesium sulfate and evaporate off the solvent to provide the title compound.

PREPARATION 12

α-Cyclopropyl-4-fluorobenzenemethanol

Add 3.2 g (0.085 mole) cyclopropyl-4-fluorobenzylmethanone to 80 ml of 3.2 g (0.085 mole) sodium borohydride partially dissolved in absolute ethanol, following the reaction by thin-layer chromatography. After about 6 hours at room temperature, cool the reaction in an ice bath and add acetic acid. Extract the mixture with methylene (3×60 ml) wash the methylene chloride extracts with saturated aqueous sodium bicarbonate solution, and dry over magnesium sulfate. Evaporate the methylene chloride extracts and dry in vacuo to yield the title compound.

PREPARATION 13

(E)-1-(4-Chloro-1-butenyl)-4-fluorobenzene

Dissolve 12.8 g (0.077 mole) of α-cyclopropyl-4-fluorobenzenemethanol in 60 ml of CHCl$_3$, add 20 ml of concentrated HCl and reflux overnight. Separate the two layers, and extract the aqueous layer with methylene chloride. Combine the methylene chloride extracts with the chloroform layer and wash with saturated aqueous sodium bicarbonate, and dry over magnesium sulfate. Evaporate the organic solvents to yield the title compound.

PREPARATION 14

1-Chloro-4-(2-propynyl)benzene

In a flask containing 59 g (2.43 mole) magnesium turnings in 500 ml anhydrous ether under an atmosphere of nitroge add slowly a solution of 465 g (2.43 mole) of 4-bromochlorobenzene in 1 liter 4 anhydrous ether. With caution, once the Grignard has started maintain slow reflux until all 4-bromochlorobenzene has been added. Stir an additional hour and then add this Grignard (maintain slow reflux) to a suspension of 170 g (2.43 mole) methoxyallene and 69 g of cuprous bromide in 300 ml anhydrous ether under N$_2$. When addition is complete, stir another 10 minutes and then add saturated ammonium chloride. Decant off the ether solution wash the solid residue with ether (3×50 ml). Combine the ether extracts and wash with 1N HCl, saturated aqueous sodium bicarbonate, water and dry over magnesium sulfate. Evaporate off the ether and distill the residue in vacuo to obtain the title compound (99–105 mmHg).

PREPARATION 15

1-(4-Chlorophenyl)-2-butyn-1-ol

Under nitrogen and with cooling, to a solution of 150.6 g (1.0 mole) 1-chloro-4-(2-propynyl)benzene in 600 ml of anhydrous ether, add dropwise 400 ml of 2.5M n-butyllithium (1.0 mole) in hexane. When addition is complete, stir a further 30 minutes and under N$_2$ add 31 g of para-formaldehyde. Stir the mixture in a dry ice/acetone bath for 1 hour. Allow to warm to room temperature and then allow to reflux. When the reaction is complete, add 400 ml of saturated aqueous sodium chloride. Separate the layers and extract the aqueous layer with ether. Wash the combined ether solution, wash with water and dry over magnesium sulfate. Evaporate off the ether, dissolve the residue in hot cyclohexane which yielded crystalline material the title compound.

PREPARATION 16

(Z)-1-(4-Chlorophenyl)-2-buten-1-ol

Under nitrogen, hydrogenate a mixture of 10 g (0.055 mole) of 1-(4-chlorophenyl)-2-butyn-1-ol and 0.6 g Lindlar catalyst. Following the reaction via NMR the reaction is complete in about two days. The hydrogenation is stopped and the reaction stirred under N$_2$ at room temperature overnight. Filter off the catalysts, wash with methylene chloride combine the filtrate and evaporate to yield the title compound.

PREPARATION 17

(Z)-4-(4-Chlorophenyl)-2-buten-1-ol 4-methylbenzenesulfonate

Dissolve 6.7 g (0.036 mole) of (Z)-1-(4-chlorophenyl)-2-buten-1-ol in 100 ml of anhydrous ether, add 3.2 g of powdered KOH. Stir the mixture and with cooling add a solution of 7.0 g p-toluenesulfonylchloride in 30 ml of anhydrous ether. Continue to stir with cooling for 30 minutes, then allow to warm to room temperature overnight. Filter, wash the filtrate three times with saturated aqueous sodium bicarbonate, then with water and dry over sodium sulfate. Evaporate off solvents and triturate residue with petroleum ether, cyclohexane. Recrystallize residue from cyclohexane to yield the title compound.

PREPARATION 18

N-Phenylmethanesulfonamide

To a 0° C. solution of 250 g (2.68 mole) of aniline and 233.2 g (2.95 mole) of pyridine in 1.25 L of methylene chloride and 319.6 g (2.79 mole) of methanesulfonyl chloride dropwise. Stir the resulting solution at 0° C. for about 30 minutes then warm to ambient temperature for about 16 hours. Extract the mixture with 2N aqueous sodium hydroxide (4×1 L). Combine the aqueous extracts and wash with 1 L of methylene chloride. Cool the aqueous layer to about 0° C. and acidify with concentrated hydrochloric acid until about pH 1. Collect the precipitate and dry to give the title compound.

NMR (DMSO-d$_6$): δ=2.97(s,3), 7.10(t,1), 7.20(d,2), 7.33(t,2), and 9.72(br s, 1)ppm.

PREPARATION 19

N-Phenylethanesulfonamide

In a manner similar to PREPARATION 18 utilize aniline +ethanesulfonyl chloride to prepare the title compound.

PREPARATION 20

N-[4-(2-Chloro-1-oxoethyl)phenyl]methanesulfonamide

In a flask containing 128.4 g (0.75 mole) of N-phenylmethanesulfonamide, 169.5 g (1.50 mole) of chloroacetyl chloride in 1 L of methylene chloride under an atmosphere of nitrogen and cooled to about −10° C. add 300 g (2.25 mole) of aluminum chloride. Stir the resulting mixture for about 16 hours. Pour the reaction mixture onto 2 Kg of ice containing 600 mL of concentrated hydrochloric acid. Collect the precipitate and wash with methanol (3×300 mL) and dry in vacuo to give the title compound.

NMR (DMSO-d$_6$): δ=3.16(s,3), 5.15(s,2), 7.40(d,2), 8.06(d,2), and 10.48 (br s, 1)ppm.

PREPARATION 21

N-[4-(3-Chloro-1-oxopropyl)phenyl]methanesulfonamide

In a manner similar to PREPARATION 20 utilizing N-phenylmethanesulfonamide +chloropropionyl chloride prepare the title compound.

EXAMPLE 1

1-[4-(4-Chlorophenyl)butyl]-3-heptylimidazolium chloride (1:1) compound with phthalic acid 1-Heptyl-1H-imidazole (6.67 g, 0.04 mole) and 4-(4chlorophenyl)butyl chloride are heated and stirred at ca. 130° C. Follow the progress of the reaction by thin-layer chromatography on silica gel (acetonitrile:ammonium hydroxide, 9:1). At the completion of the reaction, the mixture is cooled to 20°–25° C. and triturated with diethyl ether to remove any untreated starting material. The residue is dissolved in 100 ml of acetone. To the acetone solution of imidazolium salt is added a solution of phthalic acid (7.52 g, 0.045 mole) in 50 ml of acetone. The mixture is warmed to effect complete solution, then the solvent is removed in vacuo. The residue is recrystallized from acetone to provide the title compound.

NMR (DMSO-$d_6$): $\delta$=0.56–2.18(m,17), 2.64(t,2), 4.00–4.53 (m,4), ca. 5.0–ca. 9.0(broad,2), 7.09–7.50(m,4), 7.50–7.90(m,4), 7.99(m,2) and 9.70(m,1)ppm.

EXAMPLE 2

1-[3-(4-Methoxyphenyl)propyl]-3-methylimidazolium bromide

A mixture of 2.50 g (0.03 mole) of 1-methyl-1H-imidazole and 6.9 g (0.03 mole) of 1-(3-bromopropyl)-4-methoxybenzene is heated at 140° C. for 1.5 hours. Follow the progress of the reaction by thin-layer chromatography on silica gel (methanol:1M sodium chloride, 95:5). At the completion, the cooled reaction product is triturated thoroughly with ether and on drying, provides the title compound.

NMR (CDCl$_3$): $\delta$=2–2.09(m,4.5), 3.7(s,3), 4.0(s,3), 4.07–4.08(t,2), 6.6–7.2(quar.,4), 7.4–7.7 (m,2) and 10.15(s,1)ppm.

EXAMPLE 3

1-Butyl-3-[3-(4-methoxyphenyl)propyl]imidazolium bromide

A mixture of 2.5 g (0.02 mole) of 1-butyl-1H-imidazole and 4.61 g (0.02 mole) of 1-(3-bromopropyl)-4-methoxybenzene is heated at 140° C. for about 1.5 hours. Follow the progress of the reaction by thin-layer chromatography on silica gel (methanol: 1M sodium chloride, 95:5). At the completion of the reaction, the cooled reaction product is triturated thoroughly with ether and on drying, provides the title compound.

NMR(CDCl$_3$): $\delta$=1.0–3.0(m,11), 3.3–4.0(m,5), 4.2–4.8(m,4), 6.75–7.45(m,4), 7.7–7.9(bs,2) and 10.4 (s,1)ppm.

EXAMPLE 4

1-Heptyl-3-[3-(4-methoxyphenyl)propyl]imidazolium bromide

A mixture of 2.5 g (0.015 mole) of 1-heptyl-1H-imidazole and 3.45 g (0.015 mole) of 1-(3-bromopropyl)-4-methoxybenzene is heated at 140° C. for about 1.5 hours. Follow the progress of the reaction by thin-layer chromatography on silica gel (methanol: 1M sodium chloride, 95:5). At the completion of the reaction, the cooled reaction product is triturated thoroughly with ether and on drying, provides the title compound.

NMR(CDCl$_3$): $\delta$=0.8–2.8(m,19), 3.72(s,31), 4.15–4.6(m,4), 6.7–7.2(m,4), 7.5–7.75(m,2) and 10.4 (s,1)ppm.

EXAMPLE 5

1-[4-(4-Fluorophenyl)-4-oxobutyl]-3-heptylimidazolium bromide

To 3.83 g (0.019 mole) $\gamma$-chloro-p-fluorobutyrophenone add 3.19 g (0.019 mole) 1-heptyl-1H-imidazole and lower the mixture into a constant temperature bath set for 140° C. Stir the mixture for about 26 hours at this temperature. Follow the reaction progress by thin-layer chromatography on silica gel (methanol:1M sodium chloride 95:5). At the completion of the reaction, triturate the cooled oil with ethyl acetate to obtain a white crystalline solid. Dry in vacuo to obtain the title compound.

NMR(CDCl$_3$): $\delta$=0.65–1.5(br m) +1.5–3.2(br m,21), 3.8–4.1(t,2), 4.2–4.7(m,2), 6.9–7.4(br m,5) and 7.4–7.8(br m,2)ppm.

EXAMPLE 6

1-Heptyl-3-[4-(4-methoxyphenyl)butyl]imidazolium bromide

A mixture of 2.5 g (0.015 mole) of 1-heptyl-1H-imidazole and 3.66 g (0.015 mole) of 1-(4-bromobutyl)-4-methoxybenzene is heated at 140° C. for about 2 hours. Follow the progress of the reaction by thin-layer chromatography on silica gel (methanol: 1M sodium chloride, 95:5). At the completion of the reaction, the cooled reaction product is triturated thoroughly with ether and on drying, provides the title compound.

NMR(CDCl$_3$): $\delta$=0.6–2.2(m,18), 2.3–2.75(br t,2), 2.85–3.2(br s,1), 3.7(s,3), 4.05–4.48(m,4), 6.6–7.2(m,4), 7.52(br s,2) and 10.3(s,1)ppm.

EXAMPLE 7

1-Heptyl-3-[4-(4-methoxyphenyl)butyl]-2-methylimidazolium bromide

A mixture of 2.50 g (0.0139 mole) of 1-heptyl-2-methyl-1H-imidazole and 3.37 g (0.0139 mole) of 1-(4-bromobutyl)-4-methoxybenzene is heated at 140° C. for about 2 hours. Follow the progress of the reaction by thin-layer chromatography on silica gel (methanol:1M sodium chloride, 95:5). At the completion of the reaction, the cooled reaction product is triturated thoroughly with ether and on drying, provides the title compound.

NMR(CDCl$_3$): $\delta$=0.80–2.00(m,17), 2.50–2.70(t,2), 2.80(s,3), 3.80(s,3), 4.10–4.45(m,4), 6.70–7.25(m,4) and 7.70(s,2)ppm.

EXAMPLE 8

1-[3-((2,6-Dimethylphenyl)sulfamoyl)propyl]-3-heptylimidazolium chloride

Combine 15.0 g (0.0919 mole) 1-heptyl-1H-imidazole and 25.5 g (0.0974 mole) 3-chloro-N-(2,6-dimethylphenyl)propanesulfonamide and heat for about 24 hours at 130° C. Follow the progress of the reaction by thin-layer chromatography on silica gel (acetonitrile: ammonium hydroxide, 9:1). At the completion of the reaction, dissolve the resulting cooled oil in 500 ml H$_2$O. Extract the resultant solution with 6×500 ml hexane. Extract aqueous layer with 3×500 ml CH$_2$Cl$_2$. Wash combined CH$_2$Cl$_2$ layers 1×250 ml saturated NaCl solution. Dry the methylene chloride solution over Na$_2$SO$_4$. Evaporate the CH$_2$Cl$_2$ to provide the title compound as an oil. Triturate the oil with Et$_2$O to provide solid. Recrystallize by dissolving the solid in a minimum of hot acetone. Seed and chill the solution to provide white crystals.

NMR(CDCl$_3$): $\delta$=0.90–1.50(m,11), 1.5–2.1(m,2), 2.4(s,6), 2.4–3.0(m,2), 3.0–3.7(m,2), 3.9–4.3(t,2), 4.3–4.9(m,2), 7.0(s,3), 7.2(s,1), 7.89(s,1), 9.15(s,1) and 10.0(s,1)ppm.

EXAMPLE 9

1-[4-(2,3-Dichlorophenyl)-butyl]-3-heptylimidazolium chloride

A solution of 17 g (0.042 mole) 1-[4-(2,3-dichlorophenyl)-2-butenyl]-3-hepytlimidazolium chloride in 250 ml absolute ethanol and 1.5 g 10% Pd/C catalyst are placed in a small Parr bottle, and hydrogenated at 25 psi for ca. 2 hours. Additional H$_2$ is added as needed to maintain 25 psi pressure. The reaction mixture is filtered and the solvent is evaporated to provide the title compound.

NMR(CDCl$_3$): $\delta$=0.45–1.56(m,1), 1.56–2.34(m,6), 2.86(t,24.09–4.67(m,4), 6.90–7.48(m,3), 7.58(s,1) 7.74(s,1) and 10.75(s,1)ppm.

EXAMPLE 10

1-Heptyl-3-(4-phenylbutyl)imidazolium chloride (1:1 comoound with phthalic acid)

Combine 5.35 g (0.32 mole) of (4-chlorobutyl)benzene and 5.27 g (0.32 mole) 1-heptyl-1H-imidazole, stir the mixture at approximately 145° C. for about 30 hours. Follow the progress of the reaction by thin-layer chromatography on silica gel (acetonitrile:ammonium hydroxide 9:1). At the completion of the reaction, dissolve the resulting cooled oil in methanol and evaporate the solvent. Dissolve this product in 125 ml H$_2$O and extract the solution with 5×100 ml hexane. Then extract the aqueous with 2×50 ml methylene chloride. Combine the methylene chloride layers and wash with 1×100 ml saturated aqueous NaCl solution. Dry the methylene chloride extracts over sodium sulfate. Evaporate the solvents to obtain 1-heptyl-3-(4-phenylbutyl)imidazolium chloride as an oil. Dissolve the oil in approximately 35 ml acetone, and to it add an equimolar amount of phthalic acid. Remove the solvents in vacuo to obtain the title compound, which may be recrystallized from acetone.

NMR(DMSO-d$_6$): $\delta$=0.55–1.50(m,13), 1.50–2.20(m,4), 2.42–2.90(t,2), 4.00–4.55(m,4), 7.25(s,5), 7.50–7.80(m,4), 7.91(m,2), 9.65(s,1) and 10.0–13.0(bs,2)ppm.

EXAMPLE 11

1-[4-(4-Chlorophenyl)-butyl]-3-heptylimidazolium dihydrogenphosphate

Dissolve 31 g (0.084 mole) of 1-[4-(4-chlorophenyl)-butyl]-3-heptylimidazolium chloride in 70 ml of water and add to a 450 g of anion exchange resin column (Biorad AG 1-X8, hydroxide form). Elute with deionized water until the pH of eluent is about 8. Extract the combined eluent with 2×250 ml of diethyl ether. Adjust the pH of the aqueous solution to about 4 with phosphoric acid.

Remove the water in vacuo, recrystallize the solid esidue from acetonitrile, then from 2-propanol to provide the title compound.

NMR (CD$_3$OD): $\delta$=0.80–2.22(m,17), 2.70(t,2), 4.11–4.50(m,4), 7.24(s,4), 7.62–7.75(m,2) and 9.171(bs,1)ppm.

EXAMPLE 12

1-[4-[4-(Acetylamino)phenyl]butyl]-3-heptylimidazolium 4-methyl- benzenesulfonate Heat a mixture of 6.23 g (0.017 mole) 4-methylbenzenesulfonic acid 4-(4-acetylaminophenyl)butyl ester and 2.9 g (0.017 mole) 1-heptyl-1H-imidazole to 80° C., for 5 hours, following the reaction by thin-layer chromatography on silica gel (acetonitrile: ammonium hydroxide, 90:10). At the completion of the reaction, triturate the cooled resultant material with petroleum ether. Recrystallize the material from 25 ml hot methyl ethyl ketone with hot filtration, chill and seed to obtain the title compound.

NMR (DMSO-d$_6$): $\delta$=0.60–1.00(t,3), 1.00–2.00(br m,14), 2.25(s,3), 2.30(s,3), 2.35–2.70(t,2), 3.94–4.35(m,4), 6.90–7.90(m,10), 9.25(s,1) and 9.85(s,1)ppm.

EXAMPLE 13

1[3-(4-Chlorophenyl)propyl]-3-heptylimidazolium bromide

A mixture of 2.0 g (0.012 mole) of 1-heptyl-1H-imidazole and 3.0 g (0.012 mole) of 1-(3-bromopropyl)-3-chlorobenzene is heated at 115° C. for 4 hours, following the progress of the reaction by thin-layer chromatography on silica gel (methanol:1M sodium chloride 95:5). At the completion of the reaction, the reaction mixture is dissolved in water and methanol mixture and it is then washed with cyclohexane. The title compound is then extracted out of the aqueous solution with methylene chloride and obtained by removal of the methylene chloride as the hemihydrate.

NMR(cDCl$_3$): $\delta$=0.60–1.55(m, 11), 1.62–2.10(m,2), 2.10–2.60(m,2), 2.60–3.10(m,2), 4.20–4.55(m,4), 7.20(s,4), 7.42(bs,1), 7.70(bs,1) and 10.30(bs,1)ppm.

EXAMPLE 14

1-[4-(4-Chlorophenyl)butyl]-3-heptyl-2-methylimidazolium chloride (1:1 comoound with phthalic acid To 1.60 g (0.0078 mole) 1-chloro-4-(4-chlorobutyl)-benzene add 1.40 g (0.0078 mole) 1-heptyl-2-methyl-1H-imidazole. Stir the solution for one hour at about 120° C. Cool and triturate the oil with 10 ml EtOAc, followed by 2×10 ml petroleum ether, followed by 10 ml diethyl ether. Dissolve the oil in MeOH, and elute through a 1" bed of flash chromatography silica gel (Baker) with MeOH. The solvent is removed to yield an oil. Add to 0.64 g of the oil, 10 ml acetone and 0.51 g (0.0031 mole) phthalic acid. Remove the acetone in vacuo. Recrystallize the residue from acetone, filter and dry in vacuo to yield the title compound as a 1.25 hydrate.

NMR (CDCl$_3$+DMSO-d$_6$): $\delta$=0.73–2.17(br m,17), 2.73(s,3), 4.00–4.47(br m,4), 7.25(s,4) and 7.40–7.87(br m,6)ppm.

EXAMPLE 15

1-[4-(4-Chlorophenyl)butyl]-2,3-dimethylimidazolium chloride

To 4.77 g (0.023 mole) 1-chloro-4-(4-chlorobutyl)-benzene add 2.23 g (0.023 mole) 1,2-dimethyl-1H-imidazole. Stir the solution for three hours at about 115° C. Follow the progress of the reaction by thin-layer chromatography on silica gel (MeOH:NaCl(1M), 92:8). At the completion of the reaction, cool to obtain an oil.

Triturate the oil with petroleum ether until a solid precipitates. Recrystallize the solid from MeOH/acetone; filter and dry in vacuo to yield the title compound as a monohydrate.

NMR (CDCl$_3$+DMSO-d$_6$): δ=1.43–1.93(br m,4), 2.43–2.83(br m,2), 2.67(s,3), 3.83(s,3), 4.22(t,2), 7.23(s,4) and 7.72 (s,2)ppm; H$_2$O at 3.3ppm.

EXAMPLE 16

1-[2-[(2,6-Dimethylphenyl)sulfamoyl]ethyl]-3-heptylimidazolium bromide

Combine 3.46 g (0.019 mole) 1-bromoheptane and 5.16 g (0.018 mole) N-(2,6-dimethylphenyl)-2-[1H-imidazol-1-yl]ethane sulfonamide in 10 ml DMF and heat to 100° C. Follow progress of reaction by TLC on silica gel (acetonitrile:ammonium hydroxide, 9:1). After about 10 hours, allow reaction mixture to cool to room temperature. Pour the reaction mixture into 50 ml H$_2$O and extract with 1×25 ml ether to give a white precipitate in the aqueous layer. Filter and recrystallize the precipitate from acetone to provide the title compound NMR: (DMSO-d$_6$): δ=0.60–1.55(m,11), 1.55–2.05(m,2), 2.40(s,6), 3.70–4.05(t,2), 7.18(s,3), 7.85–8.10(m,2), 9.20–9.40(bs,1) and 9.50(s,1)ppm.

EXAMPLE 17

(E)-1-[4-(4-Chlorophenyl)-2-butenyl]-3-heptylimidazolium chloride (1:1) compound with phthalic acid A mixture of 1.65 g (0.01 mole) of 1-heptyl-1H-imidazole and 2.00 g (0.01 mole) of (E)-1-chloro-4-(4-chlorophenyl)-2-butene is heated at 105° C. for about two hours, following the progress of the reaction by thin-layer chromatography on silica gel (methanol:1M sodium chloride, 95:5). At the completion of the reaction, the reaction mixture is dissolved in water and it is then washed with cyclohexane. The imidazolium salt is then extracted out of the aqueous solution with methylene chloride and obtained by removing the organic solvent.

A solution of 0.39 g (2.34 mmole) of phthalic acid and 0.86 g (2.34 mmole) of (E)-1-[4-(4-chlorophenyl)-2-butenyl]-3-heptlimidazolium chloride in acetone is evaporated and then triturated with ether, filtered to obtain the title compound.

NMR (CDCl$_3$): δ=0.55–2.15(m,13), 3.20–3.45(d,2), 4.15–4.55(t,2), 4.90–5.10(d,2), 5.70–6.25(m,2), 6.90–7.40(m,10) and 10.30(s,2)ppm.

EXAMPLE 18

A. 1-[4-(4-Chlorophenyl)butyl]-3-propylimidazolium chloride

Add 7.13 g (0.035 mole) of 1-chloro-4-(4-chlorobutyl)benzene to 3.52 g (0.032 mole) of 1-propyl-1H-imidazole and heat to 130° C. for 18 hours. Follow the progress of reaction by NMR (CDCl$_3$). At the completion of the reaction, cool to room temperature to obtain the title compound.

B. 1-[4-(4-Chlorophenyl)butyl]-3-propylimidazolium dihydrogenphosphate

Dissolve 10 g (0.032 mole) of 1-[4-(4-chlorophenyl)butyl]-3-propylimidazolium chloride in water and pour onto column containing 50 g anion exchange resin (BIO-RAD hydroxide form AG-(1-X8). Elute column with water and collect eluates having pH>9. Wash these eluates with 50 ml methylene chloride. Titrate sample to pH=5 with 10% phosphoric acid and from pH=5 to pH=4.5 with 1% phosphoric acid. Evaporate aqueous solution to dryness and recrystallize from isopropyl alcohol to provide the title compound.

NMR (D$_2$O): δ=1.04(t,3), 1.35–2.38(m,6), 2.70(t,2), 4.12–4.50(m,4), 7.21(s,4), 7.43–7.66(m,2) and 7.80(br s,1)ppm.

EXAMPLE 19

A. 1-Cyclohexylmethyl-3-[4-(4-chlorophenyl)butyl]imidazolium chloride

Add 6.55 g (0.03 mole) of 1-chloro-4-(4-chlorobutyl)benzene to 4.81 g (0.293 mole) of 1-cyclohexylmethyl-1H-imidazole and heat at 130° C. for 18 hours.

Follow the progress of reaction by NMR (CDCl$_3$). At the completion of the reaction, dissolve reaction mixture in methanol: water (1:1) mixture and then wash with 260 ml cyclohexane. Extract aqueous layer with 200 ml methylene chloride and evaporate to provide the title compound.

B. 1-Cyclohexylmethyl-3-[4-(4-chlorophenyl)butyl]imidazolium dihydrogenphosphate Dissolve 7.58 g (0.021 mole) of 1-cyclohexylmethyl-3-[4-(4-chlorophenyl)butyl]imidazolium chloride in water and pour onto column containing 50 g anion exchange resin (BIO-RAD hydroxide form AG-1-X8). Elute sample through column with water and collect eluates having pH≧9. Wash these eluates with 50 ml methylene chloride. Titrate sample to pH=5 with 10% phosphoric acid and from pH=5 to pH=4.5 with 1% phosphoric acid. Evaporate aqueous solution to dryness and recrystallize from isopropyl alcohol to provide the title compound.

NMR (D$_2$O): δ=0.90–2.30(m,15), 2.68(t,2), 4.05–4.58(m,4), 7.21(s,4), 7.60(br s,2) and 8.95(br s,1)ppm.

EXAMPLE 20

1-Heptyl-3-[4-(4-methoxyphenyl)butyl]-2,4,5-trimethylimidazolium bromide

Add 3.23 g (0.0133 mole) of 1-(4-bromobutyl)-4-methoxybenzene to 2.77 g (0.0133 mole) of 1-heptyl-2,4,5-trimethyl-1H-imidazole and heat at 125° C. for two hours. Follow the progress of the reaction by thin-layer chromatography on silica gel (methanol: 1M sodium chloride, 95:5). At the completion of the reaction, dissolve the cooled reaction mixture in 100 ml water and then wash with 100 ml cyclohexane. Extract aqueous layer with 150 ml methylene chloride and evaporate to provide the title compound.

NMR (CDCl$_3$): δ=0.69–2.07(m,17), 2.30(2,6), 2.60(t,2), 2.82(2,3), 3.80(s,3), 3.95–4.35(m,4) and 6.70–7.20(m,4)ppm.

EXAMPLE 21

1-[4-(4-Chlorophenyl)butyl]-3-methylimidazolium chloride

Combine 6.1 g (0.03 mole) 1-chloro-4-(4-chlorobutyl)benzene with 2.5 g (0.03 mole) 1-methyl-1H-imidazole and heat at 120° C., following the course of the reaction by thin-layer chromatography on silica gel (methanol:1M sodium chloride, 95:5). At the completion of the reaction, cool and triturate with ether, collect the solid and recrystallize from 50 ml hot acetone to obtain the title compound.

NMR (CDCl$_3$): δ=1.35–2.30(m,4), 2.60(t,2), 4.05(s,3), 4.35(t,2), 6.80–7.80(m,6) and 10.55(s,1)ppm.

EXAMPLE 22

1-[4-(2,3-Dichlorophenyl)-2-butenyl]-3-heptylimidazolium 4-methylbenzenesulfonate 5.0 g (0.021 mole) 1-chloro-4-(2,3-dichlorophenyl)-2butene and 3.5 g (0.021 mole) 1-heptyl-1H-imidazole are dissolved in 40 ml acetonitrile and heated at reflux for about 24 hours. The reaction is followed by TLC on silica gel (EM) in acetonitrile:ammonium hydroxide, 9:1, visualized by UV and iodoplatinate. The solvent is evaporated and the residue is taken up in 100 ml H$_2$O and washed with 4×35 ml ether. To the aqueous layer is added 15 ml saturated aqueous NaCl, and the aqueous layer is extracted with 3×100 ml methylene chloride. The combined organic layers are dried over magnesium sulfate, filtered and stripped to yield an oil. The oil is chromatographed on a column prepared from a ten-fold excess of anion exchange resin (BIO-RAD 1-X8, 20–50 mesh, hydroxide form) and eluted with deionized water. The basic fractions are pooled and titrated to pH 7 with a concentrated aqueous solution of p-toluenesulfonic acid. The water is evaporated by azeotroping with acetonitrile and the resulting oil is crystallized from acetone-ether to yield the title compound.

NMR (CDCl$_3$): δ=0.54–1.45(m,11), 1.45–2.0(m,2), 2.31(s,3), 3.50(d,2), 4.15(t,2), 4.83(d,2), 5.52–6.27(m,2), 6.95–7.53(m,7), 7.75(br s,1), 7.87(br s,1) and 9.80(br s,1) ppm.

EXAMPLE 23

(±)-1-[2-Hydroxy-2-[4-[(methanesulfonyl)amino]phenyl]ethyl]-3-methylimidazolium iodide Heat a solution of 4.0 g (14.2 mmole) of (±)-N-[4-[1-hydroxy-2-(1H-imidazol-1-yl)ethyl]phenyl]methanesulfonamide, 2 ml (32.1 mmole) of iodomethane and 50 ml methanol in a glass pressure tube to 80° C. for 24 hours. Remove the solvent in vacuo. Crystallize the residue from acetone. Recrystallize from acetone to provide the title compound.

NMR (CF$_3$CO$_2$D): δ=3.2(s,3), 4.0(s,3), 4.5–5.0(m,2), 5.3–5.6(m,1), 7.2–7.6(m,6) and 8.8(m,1)ppm.

EXAMPLE 24

In a manner similar to Example 16 using acetonitrile the following compounds are prepared:

(a) 4-chloro-1-(4-chlorophenyl)-(E)-1-butene+1-heptyl-1H-imidazole=1-[4-(4-chlorophenyl)-(E)-3-butenyl]-3-heptylimidazolium chloride.

(b) 4-chloro-1-methylbutanol 4-methylbenzenesulfonate (Ester) +1-heptyl-1H-imidazole=1-[4-(4-chlorophenyl)-1-methylbutyl]-3-heptylimidazolium 4-methylbenzenesulfonate.

EXAMPLE 25

In a manner similar to Example 18 the following compounds are prepared:

(a) 1-(5-bromopentyl)-4-chlorobenzene +1-heptyl-1H-imidazole=1-[5-(4-chlorophenyl)pentyl]-3-heptylimidazolium dihydrogenphosphate.

(b) 1-chloro-4 (2 chlorophenyl)-2-buten-1-ol+1 heptyl-1H-imidazole=1-[4-(2-chlorophenyl)-2-butenyl]-3-heptylimidazolium dihydrogenphosphate.

(c) 1-chloro-4-(4-chlorobutyl)benzene+1-butyl-1H-imidazole=1-butyl-3-[4-(4-chlorophenyl)butyl]imidazolium dihydrogenphosphate.

(d) 1-chloro-4-(4-chlorobutyl)benzene+1-[4-(4-chlorophenyl)butyl-1H-imidazole=1,3-bis[4-(4-chlorophenyl)butyl]imidazolium dihydrogenphosphate.

(e) 4-(4-chlorophenyl)-3-butyn-1-ol 4-methylbenzenesulfonate (Ester)+1-heptyl-1H-imidazole=1-[4-(4-chlorophenyl)-3-butynyl]-3-heptylimidazolium 4-methylbenzenesulfonate.

EXAMPLE 26

In a manner similar to Example 20 with further conversion to the dihydrogenphosphate the following compound is prepared:

(a) 4-[(methanesulfonyl)amino]benzenebutanol methanesulfonate (Ester)+1-heptyl-1H-imidazole=1-heptyl-3-[4-[4-[(methylsulfonyl)amino]phenyl]butyl]imidazolium dihydrogenphosphate.

EXAMPLE 27

(E)-1-[4-(4-Fluorophenyl)-3-butenyl]-3-heptylimidazolium dihyrogenphosphate

Combine 4.62 g (0.025 mole) of 4-(4-fluorophenyl)-3butenyl chloride and 4.16 g (0.025 mole) of 1-heptyl-1H-imidazole and heat at 120° C. for about 8 hours, following the reaction by thin-layer chromatography. Dissolve the reaction in water and extract three times with ether. Then extract the aqueous portions with methylene chloride (10×30 ml). Wash the methylene chloride with water, dry over magnesium sulfate and then evaporate off the organic solvent. The residue is converted to the title compound as exemplified in Example 18 B.

NMR(D$_2$O): δ=0.86(t,3), 0.92–1.14(m,6), 1.14–1.30(m,2), 1.60–1.75(m,2), 2.80(q,2), 4.18(t,2), 4.46(t,2), 6.14–6.34(m,2), 7.11(dd,2), 7.40(dd,2), 7.52(s,1), 7.62(s,1) and 8.84(s,0.7)ppm.

EXAMPLE 28

(Z)-1-[4-(4-Chlorophenyl)-2-butenyl]-3-heptylimidazolium 4-methylbenzenesulfonate Add 3.37 g (0.01 mole) of (Z)-4-(4-chlorophenyl)-2-buten-1-ol 4-methylbenzenesulfonate (ester) and 1.50 g (0.009 mole) of 1-hepytl-1H-imidazole in 40 ml of acetonitrile and stir at room temperature for two days. Evaporate the acetonitrile and triturate the residue with hexanes and ethyl acetate to yield a solid. Recrystallize from ethyl acetate to provide the title compound.

EXAMPLE 29

(Z)-1-[4-(4-Chlorophenyl)-2-butenyl]-3-heptylimidazolium dihydrogenphosphate

Dissolve 2.7 g (0.005 mole) of (Z)-1-[4-(4-chlorophenyl-2-butenyl]-3-heptylimidazolium 4-methylbenzenesulfonate in 25 ml of methanol/water (80/20) mixture and pour onto column containing 8 g of anion exchange resin (BIO-RAD AG-1-X8, hydroxide form). Elute the column with water, and collect eluate having pH>8. Wash the eluate with ether. Titrate the aqueous solution to pH=5.0 with 10% phosphoric acid and from pH=5 to pH=4.5 with 1% phosphoric acid. Lyophilize to dryness and recrystallize from acetonitrile to provide the title compound.

NMR(D$_2$O): δ=0.94(t,3), 1.32(br s,8), 1.80–1.97(m,2), 3.63(d,2), 4.26(t,2), 5.05(d,2), 5.95–6.08(m,1), 6.19–6.34(m,1), 7.27(d,2), 7.40(d,2), 7.60+7.61(2s,2) and 8.76(s,1)ppm.

EXAMPLE 30

3-Methyl-1-[2-[4-((methylsulfonyl)amino)phenyl]-2-oxoethyl]-1H-imidazolium chloride Heat a mixture of 160 g (0.646 mole) of N-[4-(2-chloro-1-oxoethyl)phenyl]methanesulfonamide, 55.7 g (0.678 mole) of 1-methyl-1H-imidazole and 2.1 L of acetonitrile at reflux for about 16 hours. Cool the mixture to room temperature and collect the solid and wash with 2 L of acetonitrile. Drying provides the title compound, which may be recrystallized from aqueous ethanol.

NMR (DMSO-d$_6$): δ=3.14(s,3), 3.95(s,3), 5.98(s,2), 7.36(d,2), 7.69(t,2), 7.76(t,1), 8.02(d,2), 9.06(m,1), and 10.66(br s,1)ppm.

EXAMPLE 31

In a manner similar to EXAMPLE 30 the following compounds may be prepared:
(a) N-[4-(2-chloro-1-oxoethyl)phenyl]methanesulfonamide+1,2-dimethyl-1H-imidazole=2,3-dimethyl-1-[2-[4-((methylsulfonyl)amino)phenyl]-2-oxoethyl]-1H- imidazolium chloride
(b) N-[4-(2-chloro-1-oxoethyl)phenyl]methanesulfonamide+1-ethyl-1H-imidazole =3-ethyl-1-[2-[4-((methylsulfonyl)amino)phenyl]-2-oxoethyl]-1H-imidazol ium chloride
(c) N-[4-(2-chloro-1-oxoethyl)phenyl]methanesulfonamide+1-(1-methylethyl-1H-imidazole=3-(1-methyl-ethyl)-1-[2-[4-((methylsulfonyl)amino)-phenyl]-2-oxoethyl ]-1H-imidazolium chloride
(d) N-[4-(2-chloro-1-oxoethyl)phenyl]ethanesulfonamide+1-methyl-1H-imidazole=1-[2-[4-((ethylsulfonyl)amino)-phenyl]-2-oxoethyl]-3-methyl-1H-imidazoli um chloride
(e) N-[4-(3-chloro-1-oxopropyl)phenyl]methane-sulfonamide+1-methyl-1H-imidazole=3-methyl-1-[3-[4-((methylsulfonyl)amino)phenyl]-3-oxopropyl]-1H-imidazolium chloride

EXAMPLE 32

(±)-1-[2-Hydroxy-2-[4-((methylsulfonyl)amino)phenyl]ethyl]-3-methyl-1H-imidazolium chloride A solution of 152.3 g (0.463 mole) of 3-methyl-1[2-[4-((methylsulfonyl)amino)phenyl]-2-oxoethyl]-1H-imidazolium chloride in 1 L of distilled water and 7.62 g 10% Pd/C catalyst are placed in a 2 L Parr bottle and hydrogenated at 50 psi pressure for ca. 5 hours.

Additional H$_2$ is added as needed to maintain 50 psi pressure. The reaction mixture is filtered and the solvent is evaporated by azeotroping with ethanol to provide the title compound, which may be recrystallized from aqueous ethanol.

NMR (DMSO-d$_6$): δ=2.98(s,3), 3.87(s,3), 4.11(m,1), 4.22(m,1), 4.91(m,1), 6.10(d,1), 7.23(d,2), 7.37(d,2), 7.71(d,2), 9.16(s,1), and 9.84(s,1)ppm.

EXAMPLE 33

In a manner similar to EXAMPLE 32 the following compounds are prepared:
(a) 2,3-dimethyl-1-[2-[4-((methylsulfonyl)amino)phenyl]-2-oxoethyl]-1H-imidazolium chloride+H$_2$=(±) 2,3-dimethyl-1-[2-hydroxy-2-[4-((methylsulfonyl)a mino)phenyl]ethyl]-1H-imidazolium chloride
(b) 3-ethyl-1-[2-[4-((methylsulfonyl)amino)phenyl]-2-oxoethyl]-1H-imidazolium chloride+H$_2$=(±)-3-ethyl-1-[2-hydroxy-2-[4-((methylsulfonyl)amino)-pheny l]ethyl]-1H-imidazolium chloride
(c) 3-(1-methylethyl)-1-[2-[4-((methylsulfonyl)amino)-phenyl]-2-oxoethyl]-1H-imidazolium chloride+H$_2$=(±)-1-[2-hydroxy-2-[4-((methylsulfonyl)amino)phe nyl]ethyl]-3-(1-methylethyl)-1H-imidazolium chloride
(d) 1-[2-[4-((ethylsulfonyl)amino)phenyl]-2-oxoethyl]-3-methyl-1H-imidazolium chloride+H$_2$=(±)-1-[2-[4-((ethylsulfonyl)amino)phenyl]-2-hydroxyethyl]-3-methyl-1H-imidazolium chloride
(e) 3-methyl-1-[3-[4-((methylsulfonyl)amino)phenyl]-3-oxopropyl-1H-imidazolium chloride+H$_2$=(±)-1-[3-hydroxy-3-[4-((methylsulfonyl)amino)phenyl]propyl]- b 3-methyl-1H-imidazolium chloride

EXAMPLE 34

1-[2-(4-Aminophenyl)ethyl]-1H-imidazole

A solution of 10 g (0.046 mole) of 1-[2-(4-nitrophenyl)ethyl]-1H-imidazole in 100 mL of ethanol, 50 mL of 10% aqueous hydrochloric acid and 1.0 g of 5% Pd/C catalyst are placed in a small Parr bottle and hydrogenated at 50 psi pressure for about 24 hours. Additional H$_2$ is added as needed to maintain 50 psi pressure. The reaction mixture is filtered and the solvent is concentrated in vacuo. The residue is dissolved in 100 mL of water and made basic (pH 9) with potassium carbonate. Extract the aqueous mixture with methylene chloride (2×100 mL) and combine. Evaporation of the solvent yields the title compound.

EXAMPLE 35

1-[2-[4-[(Methylsulfonyl)amino]phenyl]ethyl]-1H-imidazole

To a −10° C. solution of 8 g (0.064 mole) of 1-[2-(4-aminophenyl)ethyl]-1H-imidazole and 10 mL triethylamine in 200 mL of methylene chloride add 5 mL of methanesulfonyl chloride dropwise. Stir the resulting solution at −10° C. for about 30 minutes then warm to ambient temperature for about 30 minutes. Wash the reaction mixture with water (2×100 mL). Extract with 10% aqueous sodium hydroxide (2×50 mL). The combined aqueous extracts are neutralized with ammonium chloride then extracted with methylene chloride (2×100 mL) and combined. Remove the solvent in vacuo to provide the title compound, which may be recrystallized from tetrahydrofuran.

NMR (CF$_3$COOH): δ=3.10–3.50(m,5), 4.40–4.80(t,2), 7.10–7.60(m,6), and 8.40(s,1)ppm.

EXAMPLE 36

3-Methyl-1-[2-[4-((methylsulfonyl)amino)phenyl]ethyl]-1H-imidazolium iodide

Heat a mixture of 5 g (0.019 mole) of N-[4-[2-(1H-imidazol-1-yl)ethyl]phenyl]methanesulfonamide, 5 mL of iodomethane and 25 mL of methanol in a pressure tube at 75° C. for about 24 hours. Cool the mixture to room temperature and remove the solvents in vacuo. Slurry the residue in acetone (50 mL) and filter and wash with acetone (100 mL). Drying provides the title compound, which may be recrystallized from methanol.

NMR (CF$_3$COOD): δ=3.15–3.55(m,5), 4.05(s,3), 4.45–4.85(t,2), 7.20–7.55(m,6), and 8.65(s,1)ppm.

EXAMPLE 37

(±)-1-[2-Hydroxy-2-[4-((methylsulfonyl)amino)phenyl]ethyl]-1H-imidazole

Heat a mixture of 30.83 g (0.097 mole) of (±)-1-[2-hydroxy-2-[4-((methylsulfonyl)amino)phenyl]ethyl-1H-imidazole hydrochloride and 5.24 g (0.097 mole) of sodium methylate in 100 mL of methanol and filter hot through 300 g of alumina (Fisher, neutral, activity III). Wash the alumina with 20% methanol in methylene chloride (200 mL). Concentrate the filtrate in vacuo to afford the title compound.

NMR (DMSO-d$_6$): δ=2.95(s,3), 4.03(m,1), 4.13(m,1), 4.79(m,1), 5.69(d,1), 6.82(s,1), 7.10(s,1), 7.16(d,2), 7.28(d,2), 7.47(s,1), and 9.74(s,1)ppm.

EXAMPLE 38

(+)-1-[2-Hydroxy-2-[4-((methylsulfonyl)amino)phenyl]ethyl]-1H-imidazole-d-7,7-dimethyl-2-oxobicyclo[2.2.1]-heptane-1-methanesulfonate Heat a mixture of 27.3 g (0.097 mole) of (±)-1-[2-hydroxy-2-[4-((methylsulfonyl)amino)phenyl]ethyl]-1H-imidazole, 22.54 g (0.097 mole) of d-7,7-dimethyl-2-oxobicyclo[2.2.1]heptane-1-methanesulfonic acid in 200 mL of water and 200 mL of ethanol to effect complete solution, then remove the solvent in vacuo. Recrystallize the residue from methanol and recrystallize the resulting crystals 3 more times from aqueous methanol to provide the title compound.

NMR (DMSO-d$_6$): δ=0.75(s,3), 1.05(s,3), 1.26–1.29(m,2), 1.83–1.93(m,2), 1.97(t,1), 2.20(m,1), 2.37(d,1), 2.98(m,1), 2.87(d,1), 2.98(s,3), 4.20–4.45(m,2), 4.92(br d,1), 5.92(br s,1), 7.20(d,2),7.35(d,2), 7.65(s,1), 7.70(s,1), 9.02(s,1), 9.77(s,1) and 14.30(br s,1)ppm. $[\alpha]_D^{23} = +14.9°$ (C, 1.95, 2N aqueous NaOH)

EXAMPLE 39

(−)-1-[2-Hydroxy-2-[4-((methylsulfonyl)amino)phenyl]ethyl]-1H-imidazole-z-7,7-dimethyl-2-oxobicyclo[2.2.1]-heptane-1-methanesulfonate Heat a mixture of 11.05 g (0.039 mole) of (±)-1-[2-hydroxy-2-[4-((methylsulfonyl)amino)phenyl]ethyl]-1H-imidazole, 9.12 g (0.039 mole) of z-7,7-dimethyl-2-oxobicyclo[2.2.1]heptane-1-methanesulfonic acid in 100 mL of water and 100 mL of ethanol to effect complete solution, then remove the solvent in vacuo. Recrystallize the residue from methanol and recrystallize the resulting crystals 3 more times from aqueous methanol to provide the title compound.

NMR (DMSO-d$_6$): δ=0.74(s,3), 1.05(s,3), 1.24–1.29(m,2), 1.76–1.82(m,2), 1.93(t,1), 2.20(m,1), 2.37(d,1), 2.67(m,1), 2.87(d,1), 2.98(s,3), 4.22–4.40(m,2), 4.92(br d,1), 5.96(br s,1), 7.20(d,2), 7.34(d,2), 7.65(s,1), 7.69(s,1), 9.01(s,1), 9.77(s,1), and 14.30(br s,1)ppm. $[\alpha]_D^{23} = -14.9°$ (C, 1.95, 2N aqueous NaOH).

EXAMPLE 40

In a manner similar to Example 37, the following compounds may be prepared:

(a) (+)-1-[2-hydroxy-2-[4-((methylsulfonyl)amino)phenyl]ethyl]-1H-imidazole-d-7,7-dimethyl-2-oxobicyclo[2.2.1]heptane-1-methanesulfonate+-sodium methylate=(−)-1-[2-hydroxy-2-[4-((methylsulfonyl)amino)phenyl]ethyl]-1H-imidazole.
$[\alpha]_D^{23} = -59.5°$ (C, 1.715, 1N aqueous HCl).

(b) (−)-1-[2-hydroxy-2-[4-((methylsulfonyl)amino)phenyl]ethyl]-1H-imidazole-z-7,7-dimethyl-2-oxobicyclo[2.2.1]heptane-1-methanesulfonate+-sodium methoxide=(+)-1-[2-hydroxy-2-[4-((methylsulfonyl)amino)phenyl]ethyl-1H-imidazole.
$[\alpha]_D^{23} = +59.7°$ (C, 1.740, 1N NaOH)

We claim:

1. A method for the treatment of cardiac arrhythmia in a mammalian subject which comprises administering to said subject an amount effective for the suppression of said arrhythmia of a compound of the formula:

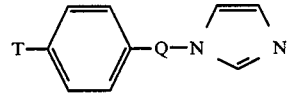

wherein T is nitro, amino, loweralansulfonamido and Q is a straight chain alkyl of 1–4 carbon atoms,

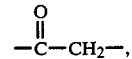

—CHOHCH$_2$—, or a pharmaceutically acceptable acid additon salt thereof.

* * * * *

UNITED STATES PATENT AND TRADEMARK OFFICE
CERTIFICATE OF CORRECTION

PATENT NO. : 4,689,341  Page 1 of 3
DATED : August 25, 1987
INVENTOR(S) : Julius Diamond, W. Lumma, T. K. Morgan, R. Wohl It is certified that error appears in the above-identified patent and that said Letters Patent is hereby corrected as shown below:

Column 4, line 33 "2oxoethyl" should read ---- 2-oxoethyl ----.

Column 5, line 19 "-CHOHCH$_2$," should read ---- -CHOHCH$_2$-, ----.

Column 11, line 43 "digitalis preoarations" should read ---- digitalis preparations ----.

Column 12, line 23 "methylene chloride" should read ---- methylene chloride. ----.

Column 12, line 32 "4-4-(acetylamino)ohenyl] should read ---- 4-[4-(acetylamino)phenyl] ----.

Column 13, line 38 "-78°C and the add" should read ---- -78°C and then add ----.

Column 14, line 2 "rate such that the methanesulfonyl chloride" should read ---- rate such that the reaction temperature does not rise beyond -5°C. After all methanesulfonyl chloride ----.

Column 15, line 25 "atmosphere of nitroge" should read ---- atmosphere of nitrogen ----.

Column 16, line 54 "mixture for about 16 hours." should read ----mixture for about 2 hours at -10°C then warm to room temperature for about 16 hours.----.

Column 17, line 7 "(4chlorophenyl)" should read ---- (4-chlorophenyl)----.

UNITED STATES PATENT AND TRADEMARK OFFICE
CERTIFICATE OF CORRECTION

PATENT NO. : 4,689,341   Page 2 of 3

DATED : August 25, 1987

INVENTOR(S) : Julius Diamond, W. Lumma, T. K. Morgan, R. Wohl

It is certified that error appears in the above-identified patent and that said Letters Patent is hereby corrected as shown below:

Column 19, line 20 "2.86 (t,24.09-4.67 (m,4)," should read
----2.86(t,2), 4.09-4.67(m,4)----.

Column 19, line 64 "esidue from acetonitrile" should read
----residue from acetonitrile----.

Column 19, line 68 "9.171(bs,1)" should read ----9.17(bs,1)----.

Column 20, line 21 "1[3-(4-" should read ---- 1-[3-(4- ----.

Column 20, line 34 "NMR (cDCl$_3$)" should read ----NMR (CDCl$_3$)----.

Column 20, line 41 "(1:1) comoound" should read ----(1:1) compound----.

Column 22, line 32 "eluates having pH $\geq$ 9" should read ----eluates having pH $\geq$ 9----.

Column 23, line 11 "2butene" should read ----2-butene----.

Column 23, line 66 "1-chloro-4 (2 chlorophenyl)" should read
----1-chloro-4-(2-chlorophenyl)----.

Column 23, line 66 & 67 "1 heptyl-1H-imidazole" should read
----1-heptyl-1H-imidazole----.

Column 24, line 26 "3butenyl" should read ----3-butenyl----.

Column 24, line 57 "[4-(4-chlorophenyl-2-butenyl]" should read
[4-(4-chlorophenyl)-2-butenyl]----.

UNITED STATES PATENT AND TRADEMARK OFFICE
CERTIFICATE OF CORRECTION

PATENT NO. : 4,689,341
DATED : August 25, 1987
INVENTOR(S) : Julius Diamond, W. Lumma, T. K. Morgan, R. Wohl It is certified that error appears in the above-identified patent and that said Letters Patent is hereby corrected as shown below:

Column 25, line 47 "3-methyl-1[2" should read ----3-methyl-1-[2----.

Column 25, line 66 "+$H_2$=($\pm$) 2,3-" should read ----+$H_2$=($\pm$)-2,3----.

Column 26, line 17 "propyl]-b3-methyl" should read ----propyl]-3-methyl----.

Column 27, line 25 "2oxobicyclo" should read ----2-oxobicyclo----.

Column 27, line 40 "imidazole-z-7,7-" should read ----imidazole-1-7,7- ----.

Column 27, line 44 "(0.039 mole) of z-7,7" should read ----(0.039 mole) of 1-7,7----.

Column 28, line 22 "1H-imidazole-z-7,7" should read ----1H-imidazole-1-7,7----.

Column 28, line 38 "loweralansulfonamido" should read ----lower alkansulfonamido----.

Signed and Sealed this

Fifth Day of April, 1988

Attest:

DONALD J. QUIGG

Attesting Officer

Commissioner of Patents and Trademarks